United States Patent [19]

May et al.

[11] 4,348,397

[45] Sep. 7, 1982

[54] PROBENECID-DYPHYLLINE THERAPY

[75] Inventors: David C. May; Charles H. Jarboe, both of Louisville, Ky.

[73] Assignee: Research Corporation, New York, N.Y.

[21] Appl. No.: 246,661

[22] Filed: Mar. 23, 1981

[51] Int. Cl.³ ............... A61U 31/19; A61U 31/52
[52] U.S. Cl. ............................ 424/253; 424/317
[58] Field of Search ......................... 424/253, 317

[56] References Cited
PUBLICATIONS

Chem. Abst., Chem. Sub Index, A–Cg (vol.-91), Benzoic Acid-4-Dipropylomine Sulfonyl.

Chem. Abst., Chem. Sub Index, 9th Collective 2--Propenenitrile, Acetyl-Pyridine, boryl. p. 33153CS.

*Primary Examiner*—Stanley J. Friedman
*Attorney, Agent, or Firm*—Omri M. Behr

[57] ABSTRACT

There is provided a method of enhancing the retention of dyphylline in the human system. Dyphylline is a known bronchodilator whose pharmacological utility has been considerably restricted by its short in vivo half life. The retention of dyphylline in the system has been enhanced by coadministration of probenecid. The utility of dyphylline in asthma therapy is therefore considerably enhanced.

8 Claims, 2 Drawing Figures

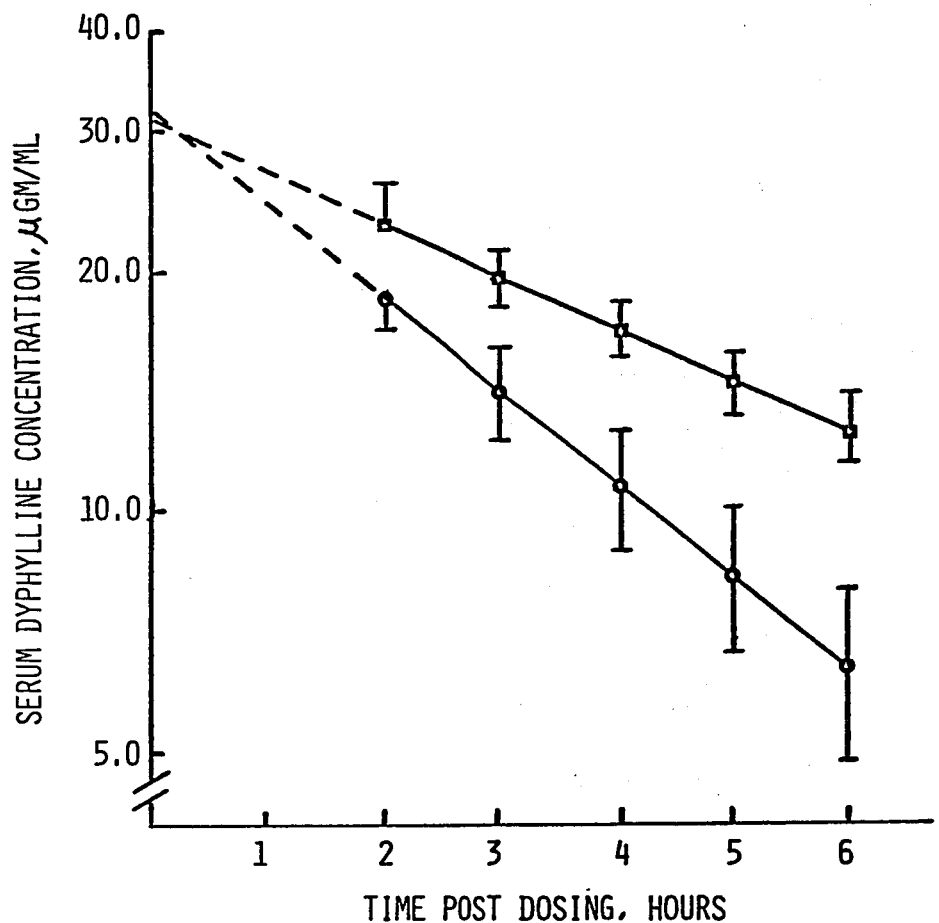
FIG. 1 MEAN DYPHYLLINE ELIMINATION CURVE BEFORE AND AFTER PROBENECID TREATMENT
Circles represent the mean serum dyphylline concentration of control determinations and squares represent mean concentrations for treatment determinations. Error bars represent standard deviation.

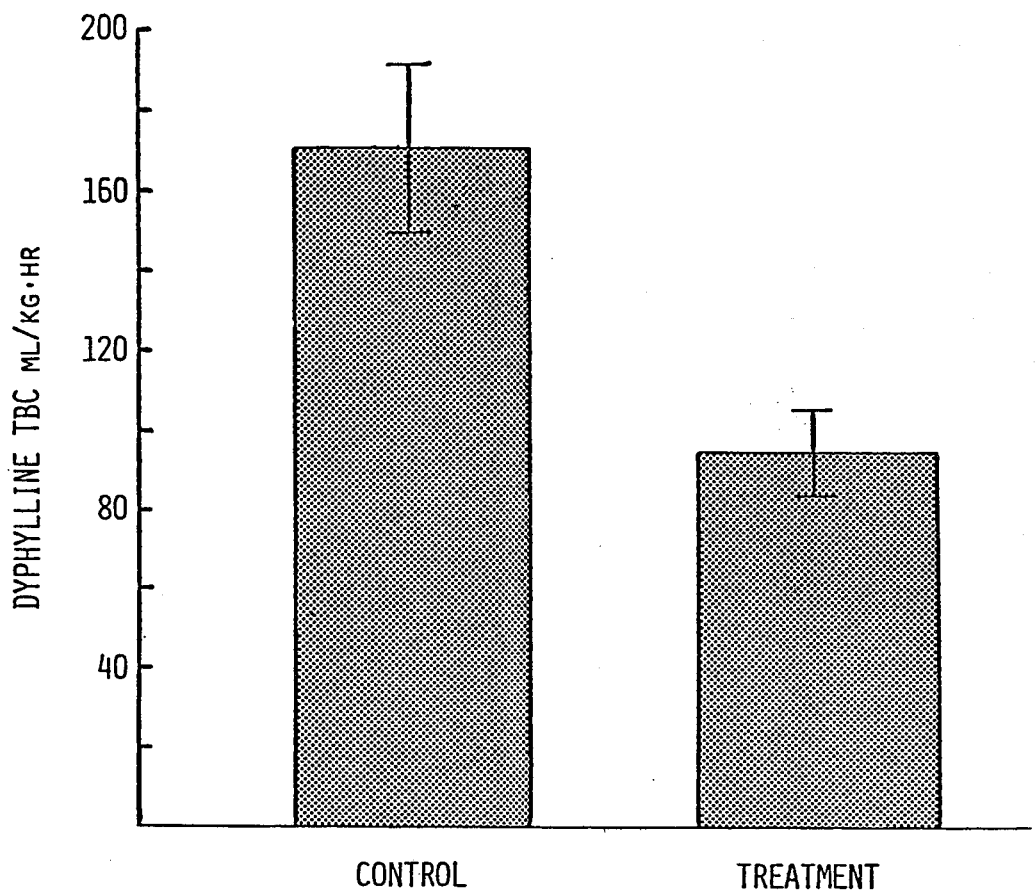
FIG. 2 COMPARISON OF DYPHYLLINE TBC VALUES FOR CONTROL AND PROBENECID TREATED HUMANS
Error bars represent standard deviation.

PROBENECID-DYPHYLLINE THERAPY

BACKGROUND OF THE INVENTION

Theophylline or 1,3-dimethylxanthine is well known as a useful vasodilator and has been used as a bronchodilator. Unfortunately, the use of this agent has been restricted because of adverse reactions in aminophylline hypersensitive patients. It has also been known to incapacitate patients to whom it is administered because of gastrointestinal side effects. Dihydroxy propyl theophylline or dyphylline is of pharmacological interest because of its relative lack of toxicity and relative freedom from the side effect of theophylline itself. Unfortunately, however it is known that dyphylline is extremely rapidly passed through the human system and 83% of an administered dose has been found to be excreted, unchanged in the urine (Simons K.J., Simons F.E.R,. J. Pharm. Sci., 1979; 68:1327-28.)

While dyphylline has been marketed as a bronchodilator this extremely rapid, substantially non metabolizing, elimination has severly restricted the use of this very valuable agent.

The metabolization of theophylline itself is quite different. Examination of the urine samples of persons to whom theophylline has been administered show virtually complete metabolization of this agent (Monks T.J., Caldwell J., Smith R.L. Clin. Pharmacal. Ther., 1979; 26:513-24.)

Probenecid is a uricosuric and renal tubular blocking agent. It has been reported to inhibit the renal transport of various types of pharmacologically active compounds (see PDR 33rd Edition, 1979 pages 1114–1142). The prime purpose of probenecid is in gout therapy for enhancing the elimination of uric acid. Theophylline as well as being a broncho and vasodilator has useful diuretic properties. Certain studies were performed (Matheson L.E., Jr., Brighley L., Hendles L. Am. J. Hosp. Pharm., 1977; 34:496-99.) to determine the blood serum levels of patients to whom theophylline and probenecid had been administered. It will be understood that in gout patients administration of a diuretic together with administration of an agent, such as probenecid, which increases the urinary excretion of uric acid would be considered as a desirable form of therapy. These studies were carried out utilizing techniques which, it was later found, gave falsely high readings of theophylline concentration in the presence of benemid. Since, as stated heretofore theophylline is substantially completely metabolized there was no intention of enhancing the retention of theophylline in the system by co-administration of probenecid.

SUMMARY OF THE INVENTION

It has been found that by substantially co-administring dyphylline and probenecid the half life of dyphylline in the human system can be substantially increased. It has been found that such a degree of increase lies between about 30 and about 70%. The ratio of the two compounds is suitably between 3 and 25 milligrams per kilograms body weight of dyphylline per 5 to 20 milligrams per kilogram of probenecid.

DESCRIPTION OF THE PREFERRED EMBODIMENTS

The retention of dyphylline in the human system may be enhanced by the administration of an retentively effective amount of probenecid to said system. The effect of enhancing the aforesaid retention is to enhance the bronchodilator action of dyphylline. Since it has been shown that dyphylline passes very rapidly through the human system it is preferred to administer the probenecid at a point in time very close to the administration of dyphylline. Thus the probenecid may be administered prior to the dyphylline, at the same time as the dyphylline or shortly thereafter. It is especially preferred though by no means critical, to administer the probenecid prior to administration of the dyphylline. Administration during a time range of between 1 hour preferably ½ hour prior, to about ½ an hour after administration of dyphylline is satisfactory. Since probenecid reaches its peak serum levels about 45 minutes after oral administration, administration 30 minutes before dyphylline is especially preferred.

Both the dyphylline and the probenecid may be administered by any mode or in any vehicle suitable to these materials. Included in such vehicles are tablets, powders, capsules, elixir, and solutions or suspensions suitable for injection. While probenecid is usually administered in the form of tablets, the mode of administration of the dyphylline will depend upon the nature of the patient and the acuteness of the condition to be remedied. Under normal circumstances administration would be in the form of tablets or capsules, however, where the patient is, say, a child or a person unable to readily swallow tablets, elixir administration is preferred. On the other hand if the condition is one which requires very rapid physiological response then administration may be by intramuscular injection.

The carriers, where present, and the dosage amounts of both the dyphylline and the probenecid are well known in the art and are available in the channels of commerce.

The amount of either of the agents will depend not only upon the body weight of the subject to whom they are administered but also the nature of the therapy which it is desired to conduct. Thus, a far higher dosage would be required in the case of the treatment of an acute attack of, say, asthma where the patient's blood levels must be rapidly loaded with the agents in question than where the purpose is merely the maintenance of a patient in stable condition, where much lower doses are required. These ranges may lie between about 3 and about 25 milligrams per kilogram of patients body weight of diphylline and between about 5 and 20 milligrams per kilogram of body weight of probenecid. These ranges should merely be regarded as operative rather than critical. Dosage ranges at the higher end of this range are preferred as initial dosage for acute attacks whereas dosages at the lower end of the range are preferred for maintenance purposes thereafter.

By utilizing the combination of dyphylline and probenecid in accordance with the procedure of the present invention the dosage interval can be raised to between about 6 to about 8 hours per administration.

While from the point of view of maximum efficiency in metabolization, pre-administration of the probenecid is desirable, such a course of action may not be preferred in a non-hospital environment. The use of a single dosage unit comprising dyphylline and probenecid and the composition of such a dosage unit in itself is within the scope of the present invention.

The compositions of the present invention may be formulated as pharmaceutical compositions which comprise, as active ingredient, dyphylline and probenecid in admixture or conjunction with a pharmaceutically acceptable carrier.

Such pharmaceutical compositions are preferably in a form suitable for buccal, parenteral, or sublingual administration. For example, they may be in the form of tablets, coated tablets, dragees, pills, capsules, drinkable suspensions, solutions or syrups or sublingual tablets.

The posology may vary over a wide range depending on the age and weight of the patient and the nature of that patients immediate physiological need.

The combination compositions in tablets of capsule form may suitably comprise between 15 and 500 mg each of dyphylline and probenecid. The dosage units should comprise substantially equal weights of both components. Nevertheless, in view of the somewhat reduced efficacy resulting from simultaneous co-administration over preadministration of probenecid, a slight excess, say, a 25 to 50% excess of dyphylline is desirable but not critical. Thus, a typical dose for treatment of an acute asthmatic condition in an adult may contain between about 300 and about 450 milligrams of dyphylline and about 300 mg of probenecid. One or two such doses may be simultaneously administered.

This problem may also be overcome by use of an excess of probenecid, say up to a 250% excess by weight.

On the other hand maintenance doses for children capable of swallowing tablets may contain as little as about 15 mg of each component.

Where administration in elixir form is desired, the carrier should contain between 10 and 15 milligrams of dyphylline and about 10 milligrams of probenecid per milliliter of elixir solution or suspension.

The combination compositions may be administered at intervals of about 6 to 8 hours. In the case of an acute attack, administration at the high end of the dosage range is provided followed by dosage at the maintenance level thereafter.

BRIEF DESCRIPTION OF THE DRAWINGS

FIG. 1 is a graph of mean dyphylline elimination curve before and after probenecid treatment.

FIG. 2 is a diagrammatic comparison of dyphylline TBC values for control and probenecid treated humans.

EXAMPLES

Protocol: This study was carried out in a cross-over fashion with each drug preparation given as a single oral dose.

On day 1, six subjects (3 male and 3 female) received dyphylline elixIr, 20 mg/kg orally, (Ariet ®. Mead Johnson) and six received proberecid (Benemid ®, Merck, Sharp and Dohme), 1 gram orally, followed in 0.5 hours by a 20 mg/kg oral dyphylline dose. Blood samples of 3 milliliters each were obtained 2,3,4,5 and 6 hours following the dyphylline dose. These were used to determine elimination kinetic parameters.

On a separate day, 48 hours removed from the initial determination, each subject received the alternate dosing regimen to complete the crossover format and blood samples were obtain vide supra.

Determination of Pharmacokinetic Parameters

Elimination phase pharamacokinetic parameters were determined in the following manner. Following quantification of the agent, a log concentration versus time graph was plotted. The best line was fitted to the points by the least squares linear regression technique utilizing a pre-programmed Texas Instruments calculator (TI-55). The slope of this line gives the elimination rate constant ($k_e$). The elimination half-life ($T\frac{1}{2}$) was calculated from the relationship $$T\frac{1}{2} = 0.693/k_e$$

The concentration at zero time (Co) was found by extrapolation of the determined line. The volume of distribution ($V_D$) was determined from the relationship $$V_D = DOSE/Co.$$

A previous study has demonstrated 100% bioavailability for oral dyphylline. The total body clearnace (TBC) was calculated using the equation $$TBC = V_D \times k_e.$$

Statistical Analysis: Statistical analysis was carried out using the paired T-test.

RESULTS

The dyphilline elimination $T\frac{1}{2}$ for control determinations was $2.57 \pm 0.45$ hours (mean $\pm$ S.D.). Following 1 gram of oral probenecid the $T\frac{1}{2}$ increased to $4.8 \pm 1.2$ hours ($p < 0.001$). This is presented graphically in FIG. 1. The corresponding $k_e$ for control and treatment determinations were $0.276 \pm 0.056$ hours $^{-1}$ and $0.150 \pm 0.037$ hours $^{-1}$ respectively ($p < 0.001$).

There was no statistically significant difference between $V_D$ values for control ($572 \pm 177$ ml/kg) and treatment ($657 \pm 121$ ml/kg) determinations.

The effect of probenecid on dyphilline TBC is shown in FIG. 2. The TBC of controls was $173 \pm 20$ ml/kg.hr. This value decreased following probenecid treatment to $95 \pm 12$ ml/kg. hr ($p < 0.001$). The percentage decrease relative to control values ranged from 34.2% to 61.0%.

The dyphylline $T\frac{1}{2}$ for controls ($2.57 \pm 0.45$ hours) compares favorably with those reported previously. Additionally, the single dose dyphilline $T\frac{1}{2}$ following 1 gram of probenecid ($4.88 \pm 1.2$ hours) was equivalent to that of theophylline in children and smokers.

The TBC of dyphylline decreased from a control value of $173 \pm 20$ ml/kg.hr to $95 \pm 12$ ml/kg hr following probenecid treatment. This decrease was due to a reduction in the $k_e$ for dyphilline rather than an alteration in the $V_D$. This is in contrast to the effect of probenecid on the penicillins.

Side effects were noted by 4 subjects. Two experienced an aftertaste similar to the taste of the drug preparation for 6 hours following administration of the dyphylline dose. This occurred during both the control and treatment determinations. Two additional subjects experienced gastrointestinal cramps without nausea following dosing for the control determination. Neither experienced this problem following dosing for the treatment determination.

EXAMPLE C-1

Tablets containing 45 mg of dyphylline and 30 mg of probenecid per unit dosage:

| | |
|---|---|
| Dyphylline, pharmaceutical grade | 450g |
| Probenecid USP | 300g |
| Talc USP | 1200g |
| Calcium carbonate USP | 300g |

-continued

| | |
|---|---|
| Ethyl cellulose USP | 50g |
| Magnesium phosphate USP | 450g |
| Methyl cellulose (sold under the Trade Name of Methocel) USP for 10,000 tablets weighing about 275 mg | 25g |

EXAMPLE C-2

Tablets containing 200 mg of dyphylline and 500 mg probenecid per unit dosage:

| | |
|---|---|
| Probenecid USP | 500mg |
| Dyphylline, pharmaceutical grade | 200mg |
| Magnesium stereate USP | 20mg |
| Lactose USP | 200mg |
| Microcrystalline cellulose USP | 680mg |

EXAMPLE C-3

Tablets containing 400 mg of dyphylline and 500 mg probenecid per unit dosage:

| | |
|---|---|
| Probenecid USP | 500mg |
| Dyphylline, pharmaceutical grade | 400mg |
| Magnesium stereate USP | 20mg |
| Microcrystalline cellulose USP | 680mg |

EXAMPLE C-4

Elixir suspension containing 200 mg of dyphylline and 500 mg probenecid per unit dosage:

| | |
|---|---|
| Dyphylline, pharmaceutical grade | 200mg/15 ml |
| Probenecid USP | 500mg/15 ml |
| Ethanol USP | 2700mg/15 ml |
| Glycerin USP | 750mg/15 ml |
| Sucrose USP | 3000mg/15 ml |
| Cherry flavor | 15mg |
| Methylparabens | 45mg |
| Povidone | 300mg |
| Water USP | to 15 ml |

We claim:

1. A method of enhancing the retention of dyphylline in the human system into which it is administered which comprises administering a retentively effective amount of probenecid to said system at substantially the time of administration of the dyphylline, wherein the amount of dyphylline administered is between about 3 and about 25 milligrams per kilogram of body weight and the amount of probenecid administered is betwen about 5 and about 20 milligrams per kilogram of body weight.

2. A method according to claim 1 wherein the probenecid is administered prior to the administration of the dyphylline.

3. A method according to claim 1 wherein the probenecid is administered substantially simultaneously with the dyphylline.

4. A method according to claim 1 wherein the dyphylline and the probenecid are each administered at intervals of between about 6 and about 8 hours.

5. A method of enhancing the bronchodilatory action of dyphylline which comprises treating a human subject in need of treatment with a bronchodilator with dyphylline in the presence of a sufficient amount of probenecid to increase the retention of dyphylline in the system of said subject, wherein the amount of dyphylline administered is between about 3 and about 25 milligrams per kilogram of body weight and the amount of probenecid administered is between about 5 and about 20 milligrams per kilogram of body weight.

6. A bronchodilatorily active composition comprising dyphylline and a sufficient amount of probenecid to substantially increase the retention of dyphylline in the human system, wherein the ratio of dyphylline to probenecid lies between 1:1 and 1.5:1, by weight.

7. A composition in accordance with claim 6 comprising between 15 and 500 milligrams of each component per unit dose.

8. A composition in accordance with claim 6 wherein the ratio of dyphilline to probenecid lies between 1:1 and 1:2.5

\* \* \* \* \*

Notice of Adverse Decision in Interference

In Interference No. 101,118, involving Patent No. 4,348,397, D. May and C. Jarboe, PROBENECID-DYPHYLLINE THERAPY, final judgment adverse to patentees was rendered Feb. 15, 1985, as to claims 1-8.

[*Official Gazette April 30, 1985.*]